United States Patent
Nesta et al.

(10) Patent No.: US 10,744,076 B2
(45) Date of Patent: Aug. 18, 2020

(54) ORAL CARE COMPOSITIONS AND METHODS OF USE

(71) Applicant: Colgate-Palmolive Company, New York, NY (US)

(72) Inventors: Jason Nesta, Cedar Knolls, NJ (US); Shira Pilch, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/520,726

(22) Filed: Jul. 24, 2019

(65) Prior Publication Data

US 2019/0343739 A1 Nov. 14, 2019

Related U.S. Application Data

(62) Division of application No. 15/370,490, filed on Dec. 6, 2016, now abandoned.

(51) Int. Cl.
| | | |
|---|---|---|
| *A61K 8/25* | (2006.01) | |
| *A61K 8/23* | (2006.01) | |
| *A61K 8/27* | (2006.01) | |
| *A61K 8/81* | (2006.01) | |
| *A61Q 11/00* | (2006.01) | |
| *A61K 8/365* | (2006.01) | |

(52) U.S. Cl.
CPC ............... *A61K 8/25* (2013.01); *A61K 8/23* (2013.01); *A61K 8/27* (2013.01); *A61K 8/365* (2013.01); *A61K 8/8182* (2013.01); *A61Q 11/00* (2013.01); *A61K 2800/31* (2013.01)

(58) Field of Classification Search
CPC ............. A61K 8/11; A61K 8/02; A61Q 11/00
USPC ........................................................... 424/53
See application file for complete search history.

(56) References Cited

U.S. PATENT DOCUMENTS

| | | |
|---|---|---|
| 4,839,156 A | 6/1989 | Ng et al. |
| 4,839,157 A | 6/1989 | Mei-King Ng et al. |
| 4,897,258 A * | 1/1990 | Rudy .................. A61K 8/11 424/53 |
| 5,059,417 A | 10/1991 | Williams et al. |
| 5,122,370 A | 6/1992 | Merianos et al. |
| 5,256,402 A | 10/1993 | Prencipe et al. |
| 5,281,412 A | 1/1994 | Lukacovic et al. |
| 5,776,435 A | 7/1998 | Gaffar et al. |
| 6,261,540 B1 | 7/2001 | Nelson |
| 8,574,555 B2 | 11/2013 | James, Jr. et al. |
| 8,591,868 B2 | 11/2013 | Chopra et al. |
| 9,999,585 B2 | 6/2018 | Fei et al. |
| 2004/0202621 A1 | 10/2004 | Orlowski et al. |
| 2006/0045854 A1 | 3/2006 | Zaidel et al. |
| 2007/0071695 A1 | 3/2007 | Chopra et al. |
| 2007/0189983 A1 | 8/2007 | Gordon et al. |
| 2008/0145321 A1* | 6/2008 | Zaidel ............... A61K 8/0208 424/53 |

FOREIGN PATENT DOCUMENTS

| | | |
|---|---|---|
| RU | 2538718 | 1/2015 |
| WO | 2014/092737 | 6/2014 |

* cited by examiner

*Primary Examiner* — Walter E Webb

(57) ABSTRACT

Disclosed herein are non-aqueous dentifrice compositions comprising (i) a whitening complex comprising crosslinked polyvinylpyrrolidone complexed with hydrogen peroxide; (ii) an off-gas reducing agent selected from sodium sulfate, magnesium sulfate, citric acid and clay; and (iii) an orally acceptable carrier. Methods of making and using the compositions are also provided.

17 Claims, No Drawings

ORAL CARE COMPOSITIONS AND METHODS OF USE

FIELD

This invention relates to non-aqueous hydrogen peroxide containing oral care compositions having reduced off-gassing effects as well as to methods of using and of making these compositions.

BACKGROUND

Many individuals desire a "bright" smile and white teeth, and consider dull and stained teeth cosmetically unattractive. Thus, there is a desire for whiter teeth and one means to achieve whiter teeth is the use of tooth whitening products.

Teeth can become discolored by foods, drinks and tobacco use. Dental stains can be classified as either extrinsic, which occur on the outer surface of teeth, or intrinsic, which occur below the surface of enamel. Most abrasive containing toothpaste remove extrinsic stains. Hydrogen peroxide ($H_2O_2$) can bleach both extrinsic and intrinsic stains and so provides fast and superior whitening efficacy. The peroxide can bleach the teeth, remove stains, and kill cariogenic bacteria. However, peroxide compounds are highly reactive, and consequently difficult to formulate. Moreover hydrogen peroxide can spontaneously decompose to form oxygen gas ($O_2$) and water. The off-gas accumulation can be problematic as in storage, dentifrice containers may bloat, burst or leak, and the remaining formulation will not have enough peroxide remaining to clean and whiten teeth effectively.

To alleviate this, some dentifrices initially comprise very high levels of peroxide, which decomposes over time, so that the exact amount of peroxide delivered on application is variable and largely depends on how long and under what conditions the dentifrice has been stored. In alternative methods, the pH of the composition is decreased to an acidic range in order to increase $H_2O_2$ stability (see, for example U.S. Pat. No. 4,839,156).

Current oral care market products do not adequately address off-gassing resulting from hydrogen peroxide decomposition. Accordingly, there is a need for oral compositions having stable hydrogen peroxide formulations.

SUMMARY OF THE INVENTION

It has been surprisingly found that the inclusion of certain ingredient components within hydrogen peroxide containing dentifrices may minimize and/or eliminate off-gas production from the oral composition. Minimizing and/or eliminating of off-gas from the dentifrice formulation may increase the stability of the oral care composition. Such activity may be useful for use in prolonging the shelf-life and quality of oral care compositions.

In one embodiment, the invention is a non-aqueous dentifrice composition comprising: (i) a whitening complex comprising cross-linked polyvinylpyrrolidone complexed with hydrogen peroxide; (ii) an off-gas reducing agent selected from sodium sulfate, magnesium sulfate, citric acid and clay; and (iii) an orally acceptable carrier.

In certain embodiments, the whitening complex is present at 5 to 20% by weight of the total composition weight. In further embodiments, the off-gas reducing agent is present at 0.02 to 5% by weight of the total composition weight. In certain embodiments, the off-gas reducing agent is present at 0.05% by weight of the total composition weight. In certain embodiments, the off-gas reducing agent is selected from sodium sulfate and magnesium sulfate. In certain embodiments, the off-gas reducing agent is selected from citric acid and clay.

In certain embodiments, the dentifrice further comprises a surfactant at 1 to 3% by weight of the total composition weight. In certain embodiments, the surfactant is sodium lauryl sulfate. In certain embodiments, the sodium lauryl sulfate is present at 2% by weight of the total composition weight. In certain embodiments, the orally acceptable carrier comprises a material selected from the group consisting of adhesion agents, surfactants, peroxide activators, solvents, flavorants, sweeteners, colorants, and mixtures thereof. In certain embodiments, the dentifrice composition further comprises an abrasive. In certain embodiments, the abrasive is present at 10 to 20% by weight of the total composition weight. In certain embodiments, the composition has a pH value between 7 to 9. In certain embodiments, the carrier is at least a flavorant. In certain embodiments, the flavorant is present at 2 to 3% by weight of the total composition weight. In certain embodiments, the dentifrice further comprises additional linear and/or cross-linked polyvinylpyrrolidone.

In certain embodiments, the invention provides for a method for making a non-aqueous dentifrice composition comprising: i) a whitening complex comprising cross-linked polyvinylpyrrolidone complexed with hydrogen peroxide; ii) an off-gas reducing agent selected from sodium sulfate, magnesium sulfate, citric acid and clay; and an orally acceptable carrier; where the method comprises the steps of: a) mixing i) a whitening agent comprising cross-linked polyvinylpyrrolidone complexed with hydrogen peroxide and ii) an orally acceptable carrier; b) adjusting the pH of the composition to a pH value between 7 to 9; and c) adding an off-gas reducing agent. In certain embodiments, the method uses an off-gas reducing agent selected from sodium sulfate and magnesium sulfate. In certain embodiments, the method uses an off-gas reducing agent selected from citric acid and clay.

In a certain embodiment, the invention is a non-aqueous dentifrice composition comprising; a whitening complex comprising cross-linked polyvinylpyrrolidone complexed with hydrogen peroxide, wherein the complex is present at 10 to 15 wt %; an off-gas reducing agent selected from sodium sulfate, magnesium sulfate, citric acid and clay, wherein the off-gas reducing agent is present at 0.05 wt %; linear and/or cross-linked polyvinylpyrrolidone at 1-2 wt %; zinc oxide at 1-2 wt %; fumed silica at 1-2 wt %; and an orally acceptable carrier.

In certain embodiments, the invention is a composition obtained or obtainable by combining the ingredients as set forth in any of the preceding compositions and methods.

DETAILED DESCRIPTION

The following description of embodiment(s) of the invention is merely exemplary in nature and is in no way intended to limit the invention, its application, or uses.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used throughout, ranges are used as shorthand for describing each and every value that is within the range. Any value within the range can be selected as the terminus of the range.

Unless stated otherwise, all percentages of composition components given in this specification are by weight based on a total composition or formulation weight of 100%. The term "wt %" is an abbreviation for weight percent.

All references cited herein are hereby incorporated by reference in their entireties. In the event of a conflict in a definition in the present disclosure and that of a cited reference, the present disclosure controls.

As used herein, the term "oral composition" means the total composition that is delivered to the oral surfaces. The composition is further defined as a product which, during the normal course of usage, is not for the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, dental strips, beads, varnish, toothpowder and the like.

As used herein, the term "dentifrice" means paste, gel, or liquid formulations unless otherwise specified. The dentifrice composition can be in any desired form such, as deep striped, surface striped, multi-layered, having the gel surrounding the paste, or any combination thereof. Alternatively, the oral composition may be dual phase dispensed from a separated compartment dispenser.

The term "effective amount" as used herein means that the amount of the composition of the present invention is of sufficient quantity to achieve the intended purpose, such as, for example, to induce or cause teeth whitening in the subject.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

In preferred embodiments of this invention, the oral composition is a dentifrice. Such dentifrices may include toothpowder, a dental tablet, toothpaste (dental cream), or gel, or any other known form known to one of skill in the art.

It has been surprisingly discovered that a low concentration of certain ingredients, e.g., 0.02 to 5 wt % in one embodiment, 0.05 to 0.2 wt % in another embodiment, 0.075 to 0.15 wt %, in another embodiment, or about 0.05 wt % in another embodiment, can achieve reduction and/or elimination of off-gas production from non-aqueous dentifrice compositions containing hydrogen peroxide.

In one embodiment, the invention provides a non-aqueous dentifrice comprising a cross-linked polyvinylpyrrolidone complexed with hydrogen peroxide, an off-gas reducing agent, and an orally acceptable carrier. In certain embodiments, the off-gas reducing agent is selected from sodium sulfate, magnesium sulfate, citric acid, and clay. In certain embodiments, the dentifrice further comprises additional linear and/or cross-linked polyvinylpyrrolidone In some embodiments, the present invention provides oral care compositions comprising: a cross-linked polyvinylpyrrolidone complexed with a hydrogen peroxide, and a stabilizing amount of an additional linear and/or cross-linked polyvinylpyrrolidone, an off-gas reducing agent, an abrasive such as calcium pyrophosphate, and a humectant.

Some embodiments provide non-aqueous dentifrice compositions comprising from 5 to 20 wt cross-linked polyvinylpyrrolidone complexed with hydrogen peroxide (PVP-$H_2O_2$). Other embodiments provide oral care compositions comprising from 5 to 12 wt cross-linked polyvinylpyrrolidone complexed with hydrogen peroxide. Still other embodiments provide oral care compositions comprising from 9 to 12 wt % cross-linked polyvinylpyrrolidone complexed with hydrogen peroxide. Yet other embodiments provide non-aqueous dentifrice compositions comprising 11 wt % crosslinked polyvinylpyrrolidone complexed with hydrogen peroxide.

By exposure to aqueous environments, as in the oral cavity, the PVP-$H_2O_2$ dissociates into individual species (PVP polymer and $H_2O_2$). The PVP-$H_2O_2$ complex is generally comprised of about 80% by weight polyvinyl pyrrolidone and 20% by weight $H_2O_2$. Single phase whitening dentifrice compounds comprising PVP-$H_2O_2$ complexes are described, e.g., in WO 2007/037961, and its parent US Pub. No. US 2007/0071695, the contents of which are incorporated herein by reference.

In some embodiments, the present invention provides non-aqueous dentifrice compositions comprising from 0.03 to about 3 wt % of an additional linear and/or crosslinked polyvinylpyrrolidone. Some embodiments provide compositions comprising 1.75 wt %, by weight, of an additional linear and/or crosslinked polyvinylpyrrolidone.

The present invention provides compositions comprising an orally acceptable carrier. As used herein, an "orally acceptable carrier" refers to a material or combination of materials that are safe for use in the compositions of the present invention, commensurate with a reasonable benefit/risk ratio, with which the peroxide complex and whitening agent may be associated while retaining significant efficacy. Preferably, the carrier does not substantially reduce the efficacy of the peroxide complex or whitening agent. Selection of specific carrier components is dependent on the desired product form, including dentifrices, rinses, gels, and paints. In various embodiments, the carrier is operable to sufficiently adhere the peroxide complex against surfaces within the oral cavity to which the composition is administered, without concomitant use of a dental tray, mouthpiece, tape, or similar appliance. In various embodiments, the carrier is operable for use with a tape, tray, mouthpiece or similar appliance.

Materials among those that are useful in carriers include adhesion agents, viscosity modifiers, diluents, surfactants, foam modulators, peroxide activators, peroxide stability agents, abrasives, pH modifying agents, humectants, mouth feel agents, sweeteners, flavorants, colorants, and combinations thereof. It is understood that while general attributes of each of the above categories of materials may differ, there may be some common attributes and any given material may serve multiple purposes within two or more of such categories of materials. Preferably, such carrier materials are selected for compatibility with the peroxide complex and with other ingredients of the composition.

In various preferred embodiments, the orally acceptable carrier may comprise polymers and/or copolymers of polyethylene glycol, of ethylene oxide propylene oxide, and of silicone. If such copolymers/polymers are used, they may be selected from the commercially available materials PLURAFLO® L4370 and PLURAFLO® L1220 (available from BASF, Wyandotte, Mich., United States of America). In one embodiment such polymer and/or copolymer is an ethylene oxide, propylene oxide block co-polymer of formula (ethylene oxide)x-(propylene oxide)y wherein x is an integer of 80-150, e.g. 100-130, e.g. about 118, and y is an integer 30-80, e.g. about 60-70, e.g. about 66, having an average molecular weight of greater than 5000, e.g., 8000-13000 Da, e.g. about 9800. Block copolymers of ethylene oxide/propylene oxide are useful, but higher molecular weight, e.g., >5000 Da are preferred, e.g. including PLURACARE® L1220 (available from BASF, Wyandotte, Mich., United States of America). Low or medium molecular weight polyethylene glycol, e.g., PEG 400, PEG 600, PEG 800, PEG 1000 and mixtures thereof are also useful. It is preferred that the carrier(s) provide a dentifrice with a viscosity of about 10,000 CPS to about 700,000 CPS, preferably about 30,000 CPS to about 300,000 CPS.

The compositions of the present invention may include any dental abrasive or combination of dental abrasive agents known in the art. "Abrasive" is as used herein is meant to include materials commonly referred to as "polishing agents" as well. Suitable abrasive may include those previously considered to be incompatible in a peroxide containing formulation ("a peroxide-incompatible abrasive"). Such abrasive is one which, in an aqueous solution with hydrogen peroxide, substantially reacts with the hydrogen peroxide so as to reduce whitening efficacy of the solution.

Any orally acceptable abrasive can be used, but preferably, type, fineness (particle size) and amount of abrasive should be selected so that tooth enamel is not excessively abraded in normal use of the composition. Suitable abrasives include, without limitation, silica (i.e. in the form of silica gel, hydrated silica or precipitated silica), alumina, insoluble phosphates, calcium carbonate, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate and insoluble sodium polymetaphosphate. Average particle size of an abrasive, if present, is generally about 0.1 to about 30 μm, for example about 1 to about 20 μm or about 5 to about 15 μm. One or more abrasives are present in an abrasive effective total amount, typically about 0.1 to about 40 wt %.

In some embodiments, the invention provides a non-aqueous dentifrice comprising an abrasive, e.g., a calcium abrasive, in particular calcium pyrophosphate. In certain embodiments, the dentifrice comprises 5-25 wt % of abrasive. In certain embodiments, the dentifrice comprises 10-20 wt % of abrasive. In other embodiments, the invention provides an abrasive-free gel.

In some embodiments, the non-aqueous dentifrice contains one or more humectants. The humectant may be selected from glycerin, propylene glycol or a combination thereof. Certain embodiments provide oral care compositions comprising from about 20 to about 60 wt %, by weight, humectant. In some embodiments, the compositions comprise from 30 to about 50 wt %, by weight, propylene glycol. In some embodiments, the compositions comprise from about 1 to about 5 wt %, by weight, glycerin. In other embodiments, the compositions comprise less than 20 wt %, by weight, of a calcium abrasive. Some embodiments provide compositions comprising from about 35 to about 45 wt %, by weight, propylene glycol; from about 2 to about 3 wt %, by weight, glycerin; and less than 20 wt %, by weight, of a calcium abrasive.

The invention may contain additional whitening agents in addition to PVP-$H_2O_2$. Any whitening agent known or developed in the art may be used. Preferably, the whitening agent includes solid whitening agents and bound whitening agents which are substantially anhydrous oxygen generating compounds. Solid whitening agents useful herein include peroxides, metal chlorites, persulfate. Exemplary peroxide phases include hydroperoxides, hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include urea peroxide, glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as and perborate salts of alkali and alkaline earth metals such as lithium, potassium, sodium, magnesium, calcium and barium, and mixtures thereof. Preferred solid peroxides are sodium perborate, urea peroxide, and mixtures thereof. Suitable metal chlorites include calcium chlorite, barium chlorite, magnesium chlorite, lithium chlorite, sodium chlorite, and potassium chlorite. The whitening agent may be preferably bound. For example, peroxide may be bound to a polymer such as PVP (poly(N-vinylpyrrolidone). Suitable PVP complexes are disclosed, for example, in U.S. Pat. No. 5,122,370, the contents of which are incorporated herein by reference. In some embodiments, it may be desirable to use any known whitening agent except sodium percarbonate and/or any of the percarbonate salts.

In various preferred embodiments, the non-aqueous dentifrice comprises a substantially anhydrous orally acceptable carrier and various dentifrice ingredients to adjust the rheology and feel of the composition such as humectants, surface active agents, thickening or gelling agents, etc.

Flavorants, sweeteners, colorants, foam modulators, mouth-feel agents and others additively may be included if desired, in the composition.

The compositions of the present invention optionally comprise one or more further active material(s), which is operable for the prevention or treatment of a condition or disorder of hard or soft tissue of the oral cavity, the prevention or treatment of a physiological disorder or condition, or to provide a cosmetic benefit.

The compositions may include a stannous ion or a stannous ion source. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%.

The oral care composition can optionally include at least one orally acceptable source of fluoride ions. Any known or to be developed in the art may be used. Suitable sources of fluoride ions include fluoride, monofluorophosphate and fluorosilicate salts. One or more fluoride ion-releasing compound is optionally present in an amount providing a total of about 100 to about 20,000 ppm, about 200 to about 5,000 ppm, or about 500 to about 2,500 ppm, fluoride ions.

The compositions of the present invention optionally comprise an antimicrobial (e.g., antibacterial) agent. A further illustrative list of useful antibacterial agents is provided in such as those listed in U.S. Pat. No. 5,776,435 to Gaffar et al., the contents of which are incorporated herein by reference. One or more antimicrobial agents are optionally present in an antimicrobial effective total amount, typically about 0.05% to about 10%, for example about 0.1% to about 3%.

The compositions of the present invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the present invention optionally comprise a sialagogue or saliva-stimulating agent, an anti-plaque agent, an anti-inflammatory agent, a desensitizing.

In various embodiments of the present invention, the oral composition comprises an anticalculus (tartar control) agent. Generally, tartar control agents are categorized as being incompatible with some whitening agents, but embodiments of the present invention incorporate tartar control agents and whitening agents in a single phase whitening composition. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. In some embodiments the anticalculus agent is present at about 0.1% to about 30%. The oral composition may include a mixture of different anticalculus agents. In one preferred embodiment, tetrasodium pyrophosphate (TSPP) and/or sodium acid pyrophosphate (SAPP) are used. In the one embodiment, the anticalculus agent comprises TSPP at about 1-2% and SAPP at about 0.5 to 5%. In a second preferred embodiment, tetrasodium pyrophosphate (TSPP) and/or sodium tripolyphosphate (STPP) are used. In the second preferred embodiment, the anticalculus agent comprises TSPP at about 1-2% and STPP at about 7% to 10%.

The compositions of the present invention may comprise a surface active agent (surfactant). Suitable surfactants include without limitation water-soluble salts of ethylene-20 alkyl sulfates, sulfonated monoglycerides of C8-20 fatty acids, sarcosinates, taurates, sodium lauryl sulfate, sodium coroyl monoglyceride sulfonate, sodium lauryl sarcosinate, sodium lauryl isoethionate, sodium laureth carboxylate and sodium dodecyl benzenesulfonate, and cocoamidopropyl betaine.

The compositions of the present invention optionally comprise a thickener. Any orally acceptable thickening agent can be used, including without limitation carbomers, also known as carboxyvinyl polymers, carrageenans, also known as Irish moss and more particularly—carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, and colloidal and/or fumed silica and mixtures of the same. One or more thickening agents are optionally present in a total amount of about 0.1% to about 90%, for example about 1% to about 50% or about 5% to about 35%.

The compositions of the present invention optionally comprise one or more further active material(s), which is operable for the prevention or treatment of a condition or disorder of hard or soft tissue of the oral cavity, the prevention or treatment of a physiological disorder or condition, or to provide a cosmetic benefit.

While ingredients are sometimes identified herein by category, e.g., humectant, antioxidant, thickener, etc., this identification is for convenience and clarity, but is not intended to be limiting. All of the ingredients in the compositions may have functions in addition to their primary function, and may contribute to the overall properties of the composition, including its stability, efficacy, consistency, mouth feel, taste, odor and so forth.

In some embodiments, the surfactant is sodium lauryl sulfate (SLS).

pH modifying agents among those useful herein include acidifying agents to lower pH, basifying agents to raise pH, and buffering agents to control pH within a desired range. For example, one or more compounds selected from acidifying, basifying and buffering agents can be included to provide a pH of 2 to 10, or in various embodiments from 2 to 8, from 3 to 9, from 4 to 8, from 5 to 7, from 6 to 10, and from 7 to 9. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range.

In certain aspects, the composition may contain the following:

| Solvents | |
|---|---|
| Glycerin | 0-7%, e.g., 3-7% or about 5% |
| Propylene glycol | 20-70%, e.g., about 40-65%, or about 50-65%, or about 50-60% |
| Ethylene oxide, propylene oxide co-polymer, avg. MW >1 kDa | 5-15%, e.g., about 7-10% or about 7.5% |
| Polyethylene glycol 600 | 0-15%, e.g., about 10% |
| Off-gas reducing agents, e.g., | |
| Sodium Sulfate | |
| Magnesium Sulfate | 0.02-5.00%, e.g. 0.02-0.05% |
| Citric Acid | |
| Clay | |
| Thickeners, e.g. | |
| Fumed silica | 0-5%, e.g., about 1.5% |
| Crosslinked polyvinylpyrrolidone | 0-10% |
| Whitener | 1-3% |
| Crosslinked polyvinylpyrrolidone complexed with hydrogen peroxide | 5-20%, e.g., about 5-12% or about 9-12% |
| Abrasive | 5-25% |
| Calcium pyrophosphate | 5-45% or 10-35%, e.g., about 15% |
| Fluoride | 0-1% |
| Sodium monofluorophosphate | 0.5-1%, e.g., about 0.76% |
| Surfactant, e.g., SLS | 0-5 e.g., 0-3%, e.g., .1-3%, e.g., about 2% |
| Antioxidant | 0.01-5% |
| BHT | 0.01-0.05%, e.g., 0.03% |
| Flavorings | 0.1-5% |
| Water | <3% |
| Tartar control agent, e.g. TSPP | 0.1-5%, or 0.3-5%, e.g., about 0.3-0.5% |

Methods are provided to make a non-aqueous dentifrice composition comprising contacting a whitening complex comprising crosslinked polyvinylpyrrolidone complexed with hydrogen peroxide; an off-gas reducing agent selected from sodium sulfate, magnesium sulfate, citric acid and clay; and an orally acceptable carrier to a tooth surface, wherein the method comprises the steps of: a) mixing i) a whitening agent comprising crosslinked polyvinylpyrrolidone complexed with hydrogen peroxide and ii) an orally acceptable carrier; b) adjusting the pH of the composition to a pH value between 7 to 9; and c) adding an off-gas reducing agent.

In one embodiment, the composition remains stable when stored for at least 1 week, at least 2 weeks, at least 1 month, at least 3 months, at least 6 months, or at least 1 year prior to contacting with the tooth surface. In one embodiment, the composition is stored at room temperature.

In further embodiments, methods are provided to whiten an oral surface in a human or animal subject comprising storing in stable form a whitening oral care composition comprising a peroxide whitening agent, a peroxide incompatible abrasive, and a substantially anhydrous orally acceptable carrier; and contacting said composition with the oral surface. As used herein "animal subject" includes higher order non-human mammals such as canines, felines, and horses. The oral care composition is contacted with an oral surface of the mammalian subject to thereby whiten teeth in a highly efficacious manner, without any negative interaction between the whitening agent, the peroxide incompatible abrasive, and other ingredients.

In various embodiments, it is preferred that the oral care composition is applied and contacted with the oral surface. The dentifrice, prepared in accordance with the present invention is preferably applied regularly to an oral surface, preferably on a daily basis, at least one time daily for multiple days, but alternately every second or third day. Preferably the oral composition is applied to the oral surfaces from 1 to 3 times daily, for at least 2 weeks up to 8 weeks, from four months to three years, or more up to lifetime.

The compositions of the invention can be packaged into containers or dispensers known in the art, via means conventional in the art. In some embodiments the compositions are packaged into tubes, metal, plastic or laminated, with either screw top or flip top caps.

In some embodiments, the diameter of the top of the tube in which the composition of the present invention is packaged, expands less than 8 mm, less than 7 mm, less than 6 mm, less than 5 mm, less than 1 mm, or less than 0.1 mm after 1 week of aging at 60° C. While in other embodiments, the diameter of the top of the tube in which a composition of the present invention is packaged does not expand to a measurable extent.

EXAMPLES

Example 1—Visual and Caliper Assessment of Peroxide Formulated Dentifrices

Dentifrice off-gas production was evaluated on tubes (Catalog #, Company) filled with test dentifrice formulations and measured using a digital caliper and visual observance. Visual observance focused on bloating, open crimping or open cap. The digital caliper was used to measure changes in tubular width. Filled tubes were incubated at either 40° C. and at 75% relative humidity, 49° C. or 60° C. Complete burst rates for the formulations containing an off gas reducing agent was observed up to 20 weeks, as compared to 12 weeks for the formulation not containing a select off gas reducing agent (Example A). Further, an increase of 33% in tubular width was observed at up to 13-14 weeks when an off-gas reducing agent was present compared to 9-10 weeks for the control group (Example A).

TABLE 1

| | Formulation | | | | |
|---|---|---|---|---|---|
| Ingredient | Example A | Example B | Example C | Example D | Example E |
| Propylene Glycol | 39.91 | 39.86 | 39.86 | 39.86 | 39.86 |
| Polyethylene Glycol/Propylene Glycol 116/66 Copolymer | 10.00 | 10.00 | 10.00 | 10.00 | 10.00 |
| Polyethylene Glycol 600 | 10.00 | 10.00 | 10.00 | 10.00 | 10.00 |
| Humectant | 2.50 | 2.50 | 2.50 | 2.50 | 2.50 |
| Sodium Sulfate | 0.00 | 0.05 | 0.00 | 0.00 | 0.00 |
| Magnesium Sulfate | 0.00 | 0.00 | 0.05 | 0.00 | 0.00 |
| Citric Acid | 0.00 | 0.00 | 0.00 | 0.05 | 0.00 |
| Clay | 0.00 | 0.00 | 0.00 | 0.00 | 0.05 |
| Tetrasodium Pyrophosphate | 1.3 | 1.3 | 1.3 | 1.3 | 1.3 |
| Sodium Acid Pyrophosphate | 0.60 | 0.60 | 0.60 | 0.60 | 0.60 |
| Sucralose | 0.05 | 0.05 | 0.05 | 0.05 | 0.05 |
| Sodium Saccharin | 0.80 | 0.80 | 0.80 | 0.80 | 0.80 |
| Sodium Monofluorophosphate | 0.76 | 0.76 | 0.76 | 0.76 | 0.76 |
| Zinc Oxide | 0.30 | 0.30 | 0.30 | 0.30 | 0.30 |
| Calcium Pyrophosphate | 15.00 | 15.00 | 15.00 | 15.00 | 15.00 |
| Cross-linked PVP complexed with Hydrogen Peroxide | 11.00 | 11.00 | 11.00 | 11.00 | 11.00 |
| Cross-linked PVP | 1.75 | 1.75 | 1.75 | 1.75 | 1.75 |
| Fumed Silica | 1.75 | 1.75 | 1.75 | 1.75 | 1.75 |
| Butylated Hydroxytoluene | 0.03 | 0.03 | 0.03 | 0.03 | 0.03 |

TABLE 1-continued

| | Formulation | | | | |
|---|---|---|---|---|---|
| Ingredient | Example A | Example B | Example C | Example D | Example E |
| Flavor | 2.25 | 2.25 | 2.25 | 2.25 | 2.25 |
| Surfactant | 2.00 | 2.00 | 2.00 | 2.00 | 2.00 |

While the present invention has been described with reference to embodiments, it will be understood by those skilled in the art that various modifications and variations may be made therein without departing from the scope of the present invention.

The invention claimed is:

1. A non-aqueous dentifrice composition comprising:
   (i) a whitening complex comprising cross-linked polyvinylpyrrolidone complexed with hydrogen peroxide present in an amount ranging from 5 to 20% by weight;
   (ii) an off-gas reducing agent selected from sodium sulfate and magnesium sulfate, present in an amount ranging from 0.02% to 0.15% by weight;
   (iii) additional linear and/or cross-linked polyvinylpyrrolidone;
   (iv) an abrasive present in an amount ranging from 0.1% to 40% by weight; and
   (v) an orally acceptable carrier.

2. The dentifrice composition of claim 1, wherein said off-gas reducing agent is present at 0.05% by weight of the total composition weight.

3. The dentifrice composition of claim 2, wherein said off-gas reducing agent is sodium sulfate.

4. The dentifrice composition of claim 2, wherein said off-gas reducing agent is magnesium sulfate.

5. The dentifrice composition of claim 1, further comprising a surfactant present in an amount ranging from 1 to 3% by weight of the total composition weight.

6. The dentifrice composition of claim 5, wherein said surfactant is sodium lauryl sulfate.

7. The dentifrice composition of claim 6, wherein the sodium lauryl sulfate is present at 2% by weight of the total composition weight.

8. The dentifrice composition of claim 1, wherein said orally acceptable carrier comprises a material selected from the group consisting of adhesion agents, surfactants, peroxide activators, solvents, flavorants, sweeteners, colorants, and mixtures thereof.

9. The dentifrice composition of claim 1, wherein said abrasive is present at 10 to 20% by weight of the total composition weight.

10. The dentifrice composition of claim 9, wherein the composition has a pH value between 7 to 9.

11. The dentifrice composition of claim 8, wherein said orally acceptable carrier is at least a flavorant.

12. The dentifrice composition of claim 11, wherein said flavorant is present at 2 to 3% by weight of the total composition weight.

13. The dentifrice composition of claim 1, comprising from 8 to 12% of the whitening complex.

14. The dentifrice composition of claim 1, wherein the composition comprises from 0.03 to 3% of additional linear and/or cross-linked polyvinylpyrrolidone.

15. The dentifrice composition of claim 14, wherein the composition comprises from 1 to 2% of additional linear and/or cross-linked polyvinylpyrrolidone.

16. The non-aqueous dentifrice composition according to claim 1, wherein the off-gas production of the non-aqueous dentifrice composition is reduced or eliminated when filled in a tube.

17. A non-aqueous dentifrice composition comprising:
   (i) a whitening complex comprising cross-linked polyvinylpyrrolidone complexed with hydrogen peroxide, wherein the complex is present at 10 to 15% by weight;
   (ii) an off-gas reducing agent selected from sodium sulfate and magnesium sulfate, wherein the off-gas reducing agent is present at 0.05% by weight;
   (iii) linear and/or cross-linked polyvinylpyrrolidone present at 1-2 by weight %;
   (iv) zinc oxide present at 1-2 weight %;
   (v) fumed silica present at 1-2 weight %; and
   (vi) an orally acceptable carrier.

* * * * *